US006589788B1

(12) United States Patent
Potyrailo et al.

(10) Patent No.: US 6,589,788 B1
(45) Date of Patent: Jul. 8, 2003

(54) METHOD FOR HIGH-THROUGHPUT FLUORESCENT SCREENING OF POLYMERIZATION REACTIONS

(75) Inventors: Radislav Alexandrovich Potyrailo, Niskayuna, NY (US); Ralph Joseph May, Niskayuna, NY (US); Ronald Eugene Shaffer, Clifton Park, NY (US); John Patrick Lemmon, Delanson, NY (US); Ronald James Wroczynski, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 336 days.

(21) Appl. No.: 09/690,442

(22) Filed: Oct. 19, 2000

(51) Int. Cl.[7] .............................................. G01N 31/00
(52) U.S. Cl. ......................... 436/37; 436/164; 436/172
(58) Field of Search ........................... 436/37, 164, 172

(56) References Cited

U.S. PATENT DOCUMENTS 4,885,254 A * 12/1989 Sung ........................... 436/172
6,166,133 A * 12/2000 Catsman ....................... 525/462

FOREIGN PATENT DOCUMENTS

WO  WO 99/50335  10/1999

OTHER PUBLICATIONS

Blaser et al. "Process Analytical Chemistry", Anal. Chem., 1995, v. 67, No. 12, pp. 47R–70R.*
Rabitz et al. "General foundations of high–dimensional model representations", J. Math. Chem. (1999), 25(2,3), 197–233 (Abstract).*
Zullo et al. "Validation and verification of continuous plants operating modes using multivariate statistical methods", Comput. Chem. Eng. (1996), 20 (Suppl. $A_1$ European Symposium on Computer Aided Process Eng.–6, 1996), S683–S688 (Abstract).*
Liebich et al. "Multivariate comparison of concentration profiles in materials analysis", Mikrochim. Acta (1989), 2(1–3), 39–48 (Abstract).*
Norman S. Allen, "Analysis of Polymer Systems by Luminescence Spectroscopy", *Analysis of Polymer Systems*, Applied Science Publishers Ltd., pp. 79–102 (1982).

(List continued on next page.)

*Primary Examiner*—Jill Warden
*Assistant Examiner*—Yelena Gakh
(74) *Attorney, Agent, or Firm*—Noreen C. Johnson; Christian G. Cabou (57) ABSTRACT

The present invention is directed to a method for the rapid screening of potential reactants, catalysts, and associated process conditions. In an embodiment, the invention comprises a method for evaluating catalyst efficacy in polymerization reactions by the determination of product molecular weight and Fries products.

40 Claims, 10 Drawing Sheets

OTHER PUBLICATIONS

NS Allen, et al, "The Use of Luminescence Spectroscopy in Aiding the identification of Commercial Polymers", *Analyst*, vol. 101, pp. 260–264 (1976).

NS Allen, et al, "Luminescence Applications in Commercial Polymers", *Chemistry and Industry*, vol. 2, pp. 907–913 (1978).

MH Chipalkatti, et al, "Investigation of Polycarbonate Degradation by Fluorescence Spectroscopy and its Impact on Final Performance", *Structure–property Relations in Polymers*, Ch. 25, American Chemical Society, Washington, DC, pp. 623–642 (1993).

VF Gachkovskii, "Some Fluorescence Methods for Estimation of the Molecular Weights of Polymers", *Poly. Sci.* (USSR) pp. 2199–2205 (1965).

CE Hoyle, "Photochemistry of Bisphenol–A Based Polycarbonate: The Effect of the Matrix and Early Detection of Photo–Fries Product Formation", *J. Polym. Sci. A: Polym. Chem.*; vol. 30, pp. 1525–1533 (1992).

CE Hoyle, et al, "Solvent Effect On the Photophysics of Bisphenol–A–Based Polycarbonate and Diphenylcarbonate", *Can. J. Chem.*, vol. 73, pp. 2062–2068 (1995).

JS Humphrey, et al, "Flash Photochemical Studies of Polycarbonate and Related Model Compounds, Photodegradation vs. Photo–Fries Rearrangement", *Macromolecules*, vol. 6, pp. 305–314 (1973).

S. Pankasem, et al, "Photochemistry and Photodegradation of Polycarbonate", *Macromolecules*, vol. 27, pp. 3773–3781 (1994).

IB Rufus, et al, "Identification of Fluorescent Products Produced By the Thermal Treatment of Bisphenol–A–Based Polycarbonate", *J. Appl. Polym., Sci.*, vol. 51, pp. 1549–1558 (1994).

H. Shah, et al, "Photochemistry of Bisphenol–A–Based Polycarbonate: Early Detection of Photoproducts by Fluorescence Spectroscopy", *Macromolecules*, vol. 27, pp. 553–561 (1994).

DF Specht, "A General Regression Neural Network", *IEEE Transaction of Neural Networks*, vol. 2, pp. 568–576 (1988).

* cited by examiner

METHOD FOR HIGH-THROUGHPUT FLUORESCENT SCREENING OF POLYMERIZATION REACTIONS

BACKGROUND OF THE INVENTION

The present invention is directed to a method for high throughput screening of potential reactants, catalysts and associated process conditions. The invention is particularly advantageous for use as a method for fluorescent screening of potential reactants and catalysts in solid melt polymerization.

Since its introduction in 1970, combinatorial chemistry has become a popular research tool among scientists in many fields. Combinatorial screening has been prevalent in the pharmaceutical industry for nearly twenty years and, more recently, combinatorial screening for improved catalysts for the bulk chemical industries has enjoyed increasing popularity.

There has been, however, a lag in the development of combinatorial screening for production scale reactions. Rapid combinatorial screening of reactants, catalysts, and associated process conditions requires that a large number of reactions or catalytic systems be tested simultaneously, while still providing a meaningful correlation between test results and eventual performance in a production-scale reactor. Before the application of the combinatorial approach, catalyst testing was traditionally accomplished in bench scale or larger pilot plants in which feed to a continuous flow reactor was contacted with a catalyst under near steady-state reaction conditions. This type of test system can be difficult to reproduce at the micro-scale required for combinatorial chemistry.

Another difficulty is that for many reactions, efficient methods of product analysis have yet to be developed. For example, solid melt polymerization is typically evaluated by determining the amount of high molecular weight polymer formed. Additionally, under some conditions, polymerization is correlated to the amount of Fries rearrangement products formed. Fries rearrangement products result from the conversion of phenolic esters into corresponding ortho and para hydroxyketones as a result of the inherent stability of polybenzenoid compounds. Although the formation of Fries rearrangement products is generally indicative of successful catalysis, the formation of Fries products may reduce the overall efficiency of the reaction by utilizing reaction components required for polymerization.

Traditional techniques for measuring the molecular weight of polymers, such as size-exclusion chromatography and light scattering, require extensive and time-consuming sample preparation steps to dissolve the polymer for analysis. Similar time-consuming sample preparation is also needed for measurement of Fries rearrangement products by traditional techniques such as nuclear magnetic resonance (NMR) and high pressure liquid chromatography (HPLC). Each of these techniques are invasive and ultimately require destruction of the sample.

As the demand for bulk chemicals has continued to grow, new and improved methods of producing more product with existing resources are needed to supply the market. However, the identities of additional effective reactants and catalyst systems for these processes continue to elude the industry. What are needed are new and improved methods and devices suitable for rapid screening of potential reactants, catalysts, and associated process conditions.

SUMMARY

The present invention is directed to methods for the rapid, non-destructive screening of potential reactants and catalysts in polymerization reactions. In one aspect, the method of the present invention comprises the steps of irradiating polymerization samples with light of a defined excitation wavelength; monitoring fluorescence emitted from each of the samples; comparing the fluorescence emission from each sample to the fluorescence emission for a database of reactions which have been characterized with respect to a predetermined set of reaction parameters; and correlating the sample fluorescence with selected reaction parameters of interest. Also included in the present invention are systems for performing the method.

BRIEF DESCRIPTION OF THE DRAWINGS

Various features, aspects, and advantages of the present invention will become more apparent with reference to the following description, appended claims, and accompanying drawings, wherein:

DETAILED DESCRIPTION

Terms used herein are employed in their accepted sense or are defined. In this context, the present invention is directed to methods for rapid screening of potential reactants, catalysts, and associated process conditions.

In polymer chemistry, the need to evaluate variable concentrations of a single catalyst as well as various combinations of multiple catalysts can dramatically add to the number of catalytic materials that require testing. For example, the number of potentially useful compounds which can catalyze melt polycarbonate polymerization is approximately $10^4$. Discovery of adequate catalysts for melt polymerization will be accelerated by using combinatorial chemistry, as has been demonstrated in other systems.

In one aspect, the invention comprises a method for the rapid screening of potential reactants, catalysts and reaction conditions associated with product formation. In an embodiment, the invention relates to a method for the identification of reaction conditions which generate efficient production of high molecular weight polycarbonate. Reaction samples are irradiated with light of a defined excitation wavelength and fluorescence emission from each sample is monitored. The sample fluorescence is then compared to fluorescence emission profiles from reactions which have been characterized with respect to reaction parameters of interest. In an embodiment, the reaction parameters of interest comprise high molecular weight polymer and Fries rearrangement products.

Catalysts can be distinguished in terms of their relative activity, as well as their relative selectivity for product formation. Catalysts with high activity will generally increase the amount of all reaction products formed. Catalysts with high selectivity will enhance the formation of the intended product relative to other possible reaction byproducts. Generally, the catalysts with high efficiency will comprise high activity and high selectivity, whereas catalysts with low activity or low selectivity will not be as useful. For melt polymerization, catalyst selectivity can be measured as the amount of high molecular weight polymer formed, as compared to the amount of Fries rearrangement products formed, and is expressed as the ratio of molecular weight to Fries (Mn/Fries). Catalysts such as sodium hydroxide (NaOH) are highly active in melt polymerization, but not highly selective, in that large amounts of high molecular weight polymer and large amounts of Fries rearrangement products are formed. Catalysts such as calcium acetate $(Ca(OAc)_2)$ produce less Fries rearrangement products, but also produce less high molecular weight polymer. It will be recognized by those of ordinary skill in the art that polymer molecular weight may be expressed either as a number average molecular weight (Mn) or weight average molecular weight (Mw). Thus, catalyst selectivity may also be evaluated as the ratio of weight average molecular weight (Mw) to Fries (Mw/Fries), or the ratio of number average molecular weight to Fries (Mn/Fries).

While selectivity is an important parameter for evaluation of catalyst performance, it is also useful to individually quantify Fries and molecular weight values. This information adds to the understanding of catalyst activity. "Activity" here is defined as the ability of a catalyst to build molecular weight. Thus, in one aspect, an emission spectrum for each reaction sample may be used to assess predetermined reaction parameters related to catalyst activity. In an embodiment, the invention comprises a method for quantitation of molecular weight and Fries product simultaneously. This determination is preferably performed by collecting multiple wavelengths of fluorescence emission (more than two wavelengths) under a single or multiple excitation wavelengths and applying multivariate statistical tools (chemometrics) to extract relevant data about Fries concentration and molecular weight in analyzed material.

In an embodiment, principal component analysis (PCA) is used to describe the spectral features comprising the majority of variation of spectra from a plurality of reaction samples. Preferably, the spectral variation is correlated with reaction parameters of interest. More preferably, the reaction being evaluated is polycarbonate production and the reaction parameters of interest are polymer molecular weight and Fries rearrangement products.

In an embodiment, spectral descriptor scores are derived for reaction samples based on projection of individual spectra onto the principal components of spectral variation. Preferably, spectral descriptors from a database of known catalysts can be compared to spectral descriptors from reactions testing new catalysts to enable qualitative assessment of new catalyst performance. In one aspect, spectral descriptors for multiple loadings of a new catalyst are generated and linked together to form a spectral map. The spectral map for the new catalyst is preferably compared to a spectral map for control catalysts from the same reaction set.

The method also, provides for a quantitative assessment of the reaction parameters of interest. In an embodiment, a database of fluorescence emission spectra comprising a wide range of reaction parameters, such as Fries and polymer molecular weight, are compiled. The fluorescence emission spectrum of a sample comprising a new catalyst is compared to the database, and values for reaction parameters of interest are predicted using multivariate calibration methods preferably including, but not limited to, nearest neighbor Euclidean distance, locally weighted regression modeling, generalized regression neural network modeling, back propagation neural network, radial basis function neural network, and partial least squares regression (PLS).

Thus, the invention comprises using sample fluorescence to rapidly and non-invasively screen multiple polycarbonate polymerization reactions. In the past, fluorescence spectroscopy has been used for flash photochemical studies of polycarbonate and related model compounds (J. S. Humphrey et al., *Macromolecules* 6: 305–314 (1973)), identification of initial salicylate photo-Fries rearrangement products of polycarbonate (C. E. Hoyle et al., *J. Polym. Sci. A: Polym. Chem.* 30: 1525–33 (1992)), detection of salicylic and 2,2'-bisphenol type products in the very early stage of polycarbonate photolysis (H. Shah et al., *Macromolecules*, 27: 553–561 (1994)), investigation of solvent effects on the photophysics of bisphenol-A-based polycarbonate and diphenylcarbonate (C. E. Holyle et al., *Can. J. Chem.*, 73: 2062–68 (1995)), studies of the photochemistry and photodegradation of polycarbonate (S. Pankasem et al., *Macromolecules* 27: 3773–81 (1994)), and identification of fluorescent products produced by thermal treatment of bisphenol-A-based polycarbonate (I. B. Rufus et al., *J. Appl. Polym. Sci.* 51: 1549–58 (1994)). Studies relating luminescence to polymer molecular weight have met with limited success (see N. S. Allen, in *Analysis of Polymer Systems*, Chapter 4, Eds. L. S. Bark and N. S. Allen, Applied Science Publishers Ltd., London (1982)). For example, it has been shown that under certain conditions, polystyrene fluorescence may be inversely correlated with molecular weight (V. F. Gachkovskii, *Polym. Sci.* (USSR) 2199 (1965)), original source, *Vysokomol. Soedin.*, 7(12):2009, (1965); discussed in N. S. Allen, in *Analysis of Polymer Systems*, Chapter 4, Eds. L. S. Bark and N. S. Allen, Applied Science Publishers Ltd., London (1982)). Other studies have described the use of luminescence spectroscopy to identify and characterize commercial polymers, (see N. S. Allen and J. F. McKellar, *Chemistry and Industry*, 2:907–913 (1978)); N. S. Allen et al., *Analyst* 101:260–264 (1976); and N. S. Allen, in *Analysis of Polymer Systems*, Chapter 4, Eds. L. S. Bark and N. S. Allen, Applied Science Publishers Ltd., London (1982)); and to measure byproducts of polymer degradation (M. K. Chipalkatti and J. J. Laski, in *Structure-Property Relations in Polymers, Spectroscopy and Performance*, Chapter 25, pp 623–642, Eds: M. W. Urban and C. D. Craver, American Chemical Society, Washington, DC (1993). Also, European patent application WO99/50335 describes correlation of fluorescence intensities at two excitation wavelengths to polycarbonate quality. Although these references describe the use of fluorescence for identification of polymer byproducts and estimation of polymer molecular weight, they do not describe the simultaneous quantification of multiple parameters of interest in analyzed samples.

Figure 1:
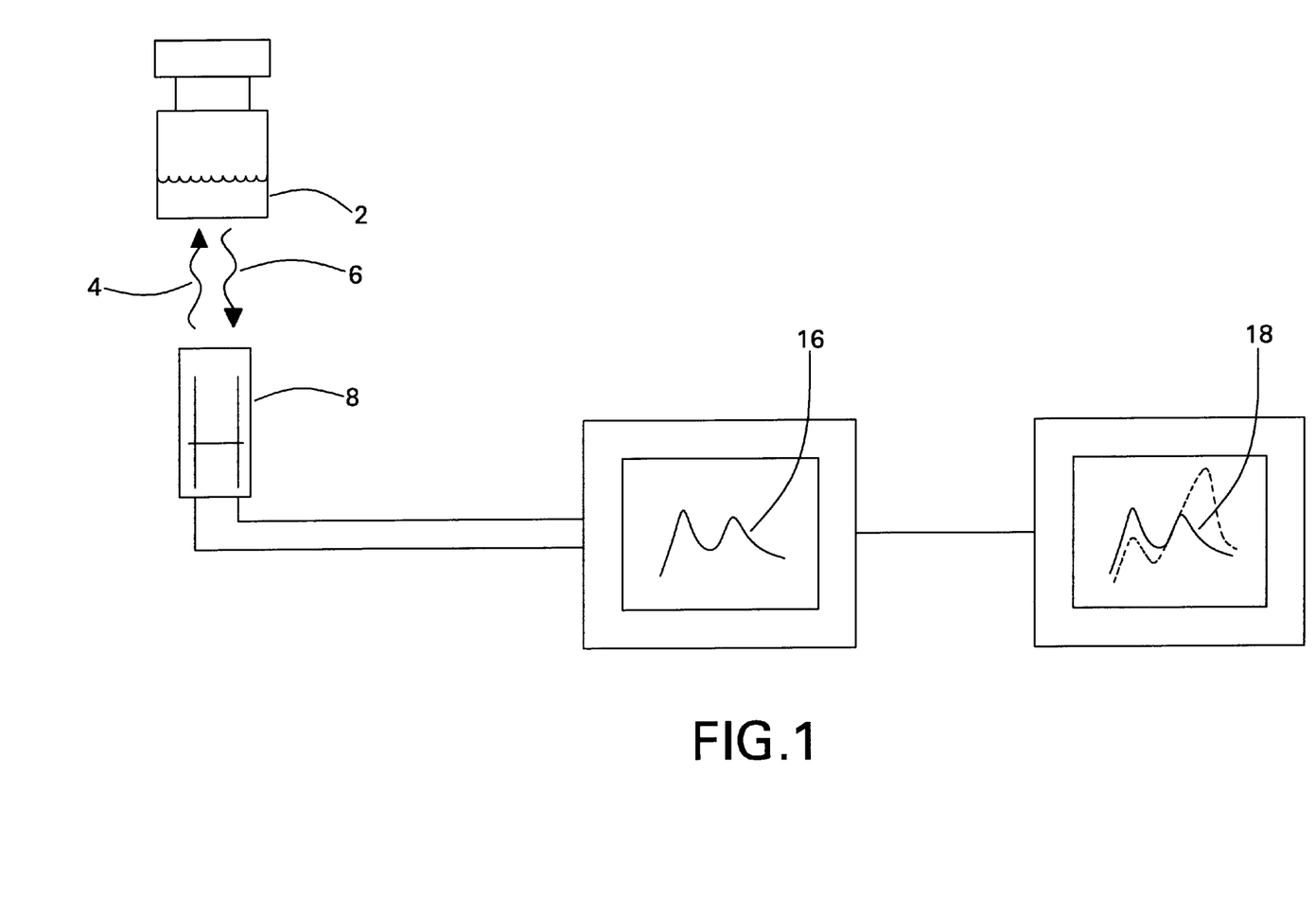
FIG. 1 is a schematic representation of one aspect of an embodiment of the invention.

Referring now to FIG. 1, a method for the determination of reaction parameters of interest comprises irradiation of samples 2 with light of a defined excitation wavelength 4. Fluorescent light 6 emitted from the irradiated samples is then collected, for example, by a probe 8, and transmitted to a spectrophotometer 10 for generation of a signal 16 characteristic of the individual sample 2. Preferably signal 16 is an emission profile for more than one predetermined wavelength, or set of wavelengths. The sample fluorescence is then compared to other fluorescence profiles in the database 18 generated from reactions which have been characterized with respect to predetermined reaction parameters of interest. Generally, the spectral emission is dependent upon the excitation wavelength employed. For example, election of spectral ranges for the excitation of polycarbonate and for collection of fluorescence emission can be complicated by the presence of multiple fluorescing species in the sample. These species can include monocapped bisphenol A (BPA), small hydroxyl terminated oligomers, cyclics and others. Preferably, excitation wavelength 4 comprises 200 to 550 nm. More preferably, excitation wavelength 4 comprises 300 to 470 nm. More preferably excitation wavelength 4 comprises 310 to 350 nm. Most preferably excitation wavelength 4 comprises 340 nm.

Figure 2:
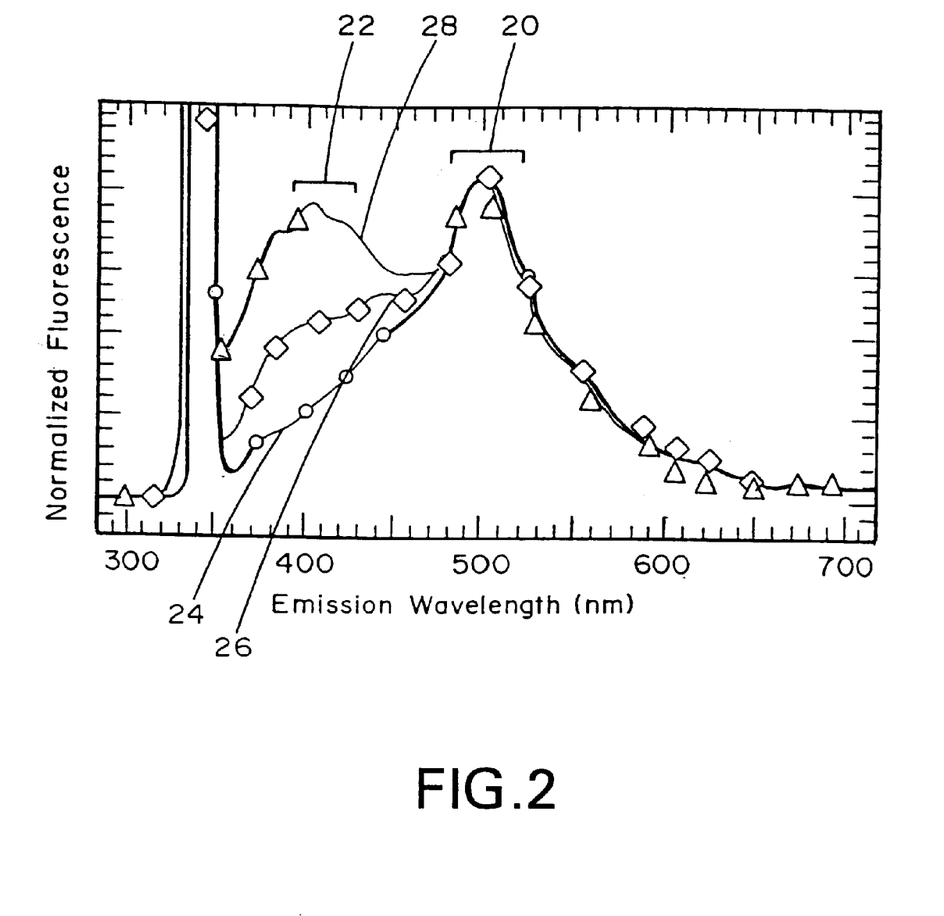
FIG. 2 is a representation of an embodiment of the invention showing fluorescence emission spectra for samples of different catalyst selectivity.

Referring now to FIG. 2, in one aspect, polycarbonate samples having different polymer molecular weight and Fries products comprise differently shaped spectra. In an embodiment, spectral changes in the fluorescence emission spectra are correlated with certain polymer byproducts and molecular weight. Thus, the size and shape of fluorescence band 22 at about 400 nm relative to the size and shape of fluorescence band 20 at about 500 nm is correlated with Fries and molecular weight in polycarbonate. Generally, multivariate statistical methods are necessary to extract multiple parameters of catalyst performance. Preferably, multivariate statistical methods relate the shape and intensity of the fluorescence spectra to Fries and molecular weight in a polycarbonate sample. For example, and referring again to FIG. 2, sample 24 exhibiting a low ratio of polymer molecular weight to Fries products preferably has a different shaped curve than sample 26 exhibiting a mid-range ratio of polymer molecular weight to Fries products or sample 28 exhibiting high ratio of polymer molecular weight to Fries products.

In another aspect, a spectrum is generated for each reaction sample. In an embodiment, a database of spectra for samples comprising a wide range of reaction parameters of interest is compiled. Preferably, the reaction parameters of interest are correlated to spectral shape. More preferably, the reaction parameters include polymer molecular weight and Fries products. The fluorescence spectrum preferably ranges from about 200 to 900 nm. More preferably, the fluorescence spectrum ranges from about 260 to 800 nm.

The spectra can be used to provide either qualitative or quantitative information regarding the reaction parameters of interest.

In one aspect, principal components analysis of fluorescence emission spectra from a plurality of polymerization reactions is described. Preferably, an emission spectrum for each sample is represented as a single spectral descriptor comprised of principal component scores that are derived from the principal components which describe the majority of spectral variation for that spectrum. More preferably, the spectral variation is correlated with reaction parameters of interest. Even more preferably, spectral descriptors for a new sample are compared to spectral descriptors from a database comprising a plurality of reactions which have been characterized regarding reaction parameters of interest, and used to qualitatively predict selected reaction parameters for the new sample.

Spectral descriptors are preferably derived using a variety of multi-dimensional statistical tools such as principal components analysis and non-linear mapping. Principal component analysis attempts to find a new lower-dimensional coordinate system that captures the variance in the original data. The first principal component is the axis along the direction of the primary source of variation; the second principal component is the axis along the second most major source of variation; the third principal component is the axis along the third most major source of variation, and so forth. Because polycarbonate fluorescence emission spectra are fairly simple, the majority of spectral variation is generally described using the first two or three principal components.

Thus, in an embodiment, principal component scores for a spectrum are computed by projecting the spectrum into a coordinate system which is defined by the major principal components calculated for a database of spectra. Preferably, the database comprises a plurality of reactions which have been characterized with respect to at least one reaction parameter of interest. Even more preferably, the reaction is polymerization, and the reaction parameters of interest are Fries and polymer molecular weight.

In an embodiment, plotting the spectral descriptors as a function of their principal component scores generates a two-dimensional spectral descriptor plot. The spectral descriptor plot enables the direct comparison of all the spectra in the database. Because the position of each spectral descriptor in the plot is defined by the major components of variation in the spectra, spectra of similar shape will preferably generate spectral descriptors which fall near each other in the spectral plot. Conversely, spectra of dissimilar shape will preferably generate spectral descriptors which fall far from each other in the spectral plot. For example, spectral descriptors characteristic of samples with large molecular weight polymers are distinguished from samples with low molecular weight polymers. Similarly, samples with high amounts Fries products are distinguished from samples with low amounts of Fries products.

Figure 3:
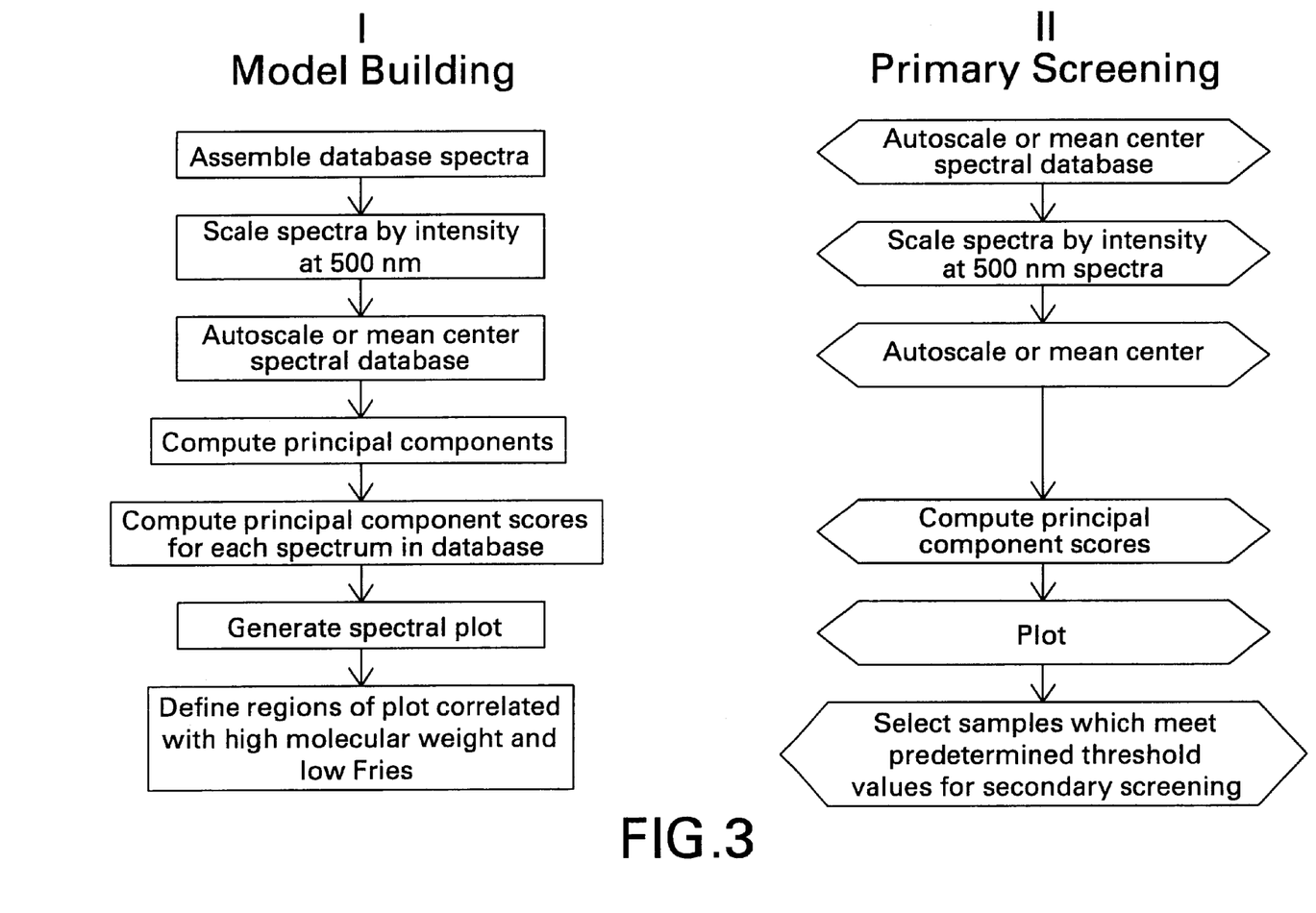
FIG. 3 is a schematic representation of an embodiment of the method of using of spectral descriptors as a primary screening tool.

Referring now to FIG. 3, in an embodiment, the method comprises two general phases: (I) model building, followed by (II) primary screening of new catalysts.

Preferably, model building comprises assembling a database of samples which have been characterized with regard to reaction parameters of interest, such as Fries and polymer molecular weight. Thus, in an embodiment model building comprises: (1) assembling a database or calibration set covering a wide range of polycarbonate material with known levels of Fries and molecular weight; (2) normalization or scaling the spectra, as for example, to a relative intensity of 1.0 at 500 nm; (3) preprocessing of the database spectra, as for example, by auto-scaling or mean centering; (4) computing principal components associated with spectral variation using principal component analysis; (5) deriving spectral descriptor "scores" for each of the database spectra by projecting each of the database spectra into a two-dimensional coordinate system defined by the principal components; (6) plotting the database spectral descriptors as a function of their scores to generate a spectral descriptor plot; and (7) defining regions in the spectral descriptor plot that correlate with samples having high molecular weight polymer and low Fries products. It will be recognized by those of ordinary skill in the art that the steps of normalizing individual spectra with respect to each other, and preprocessing of the database, are optional in that they are not necessarily required for all applications.

Figure 4:
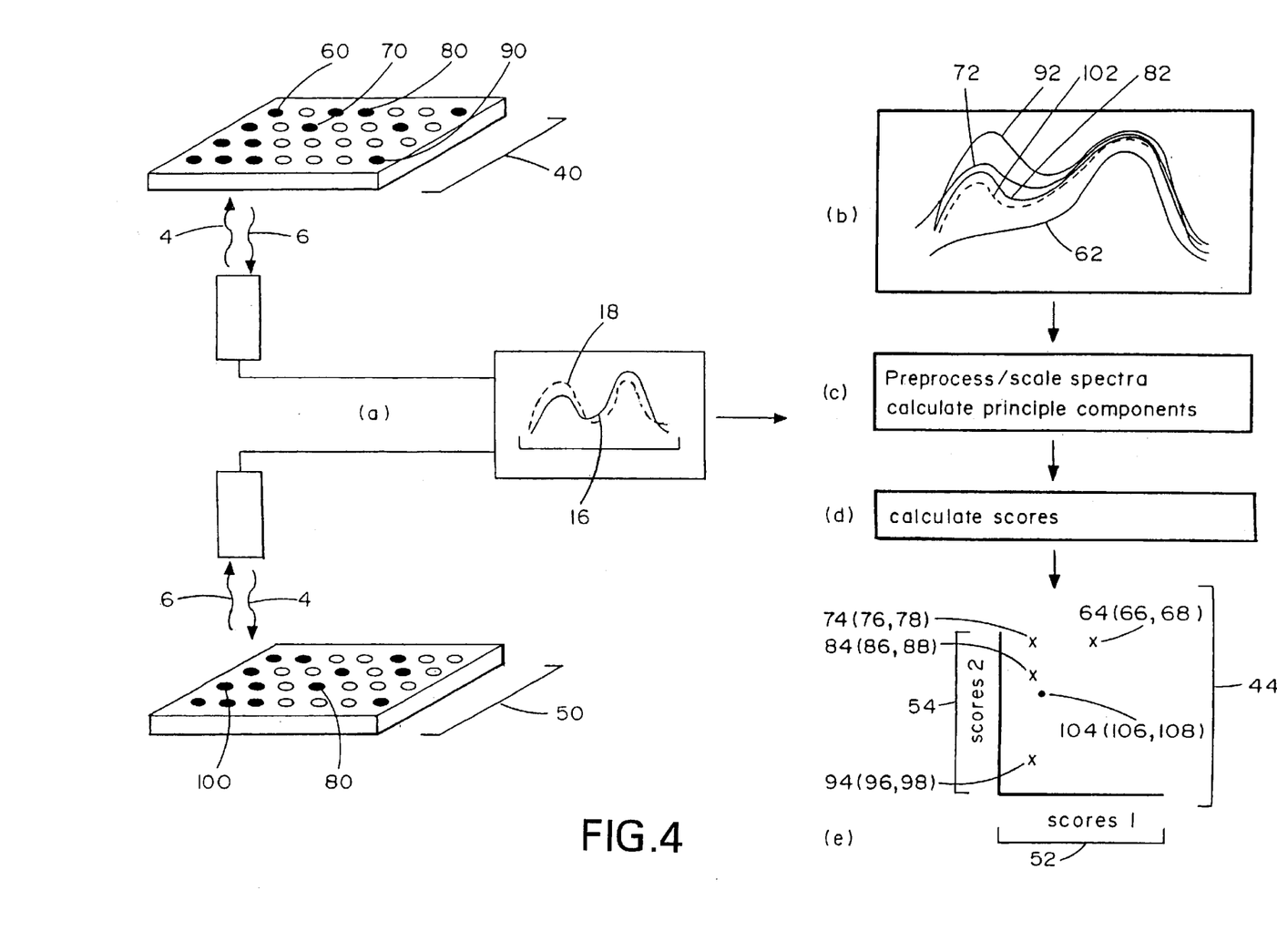
FIG. 4 is a schematic representation of an embodiment of the method of generating spectral plots.

Referring now to FIG. 4, in an embodiment, samples 40 are irradiated with light 4 of a defined wavelength to generate a spectrum for each sample (step a). If necessary, the individual spectra are scaled, as for example, to a relative value of 1.0 at 500 nm (step b), and principal components associated with the majority of spectral variation are computed by principal component analysis (step c). Spectral descriptor "scores" for each spectrum in the database are then calculated by projecting each spectrum onto the coordinate system defined by the principal component analysis (step d). Preferably, each spectral descriptor score is correlated to Fries products and polymer molecular weight. Spectral descriptors are then plotted (step e) based on score values, and plots 44 used to distinguish samples having low molecular weight polymer 64 from samples having high molecular weight polymer 84, and samples having high amounts of Fries products 64 from samples having a low amounts of Fries products 74.

Thus, spectral plot 44 comprises a two-dimensional plot of spectral descriptors. Each spectral descriptor comprises individual scores 52 and 54 which describe the majority of spectral variation associated with the original spectrum 16 for each sample. For example, spectral descriptor 64 from sample 60 and spectrum 62 comprises a point on spectral plot 44 based on score values 66 and 68; spectral descriptor 74 from sample 70 and spectrum 72 preferably comprises a point on spectral plot 44 based on score values 76 and 78; spectral descriptor 84 from the test sample 80 and spectrum 82 preferably comprises a point on spectral plot 44 based on score values 86 and 88, and so forth. In a preferred embodiment, spectra 72 and 82 that have similar shapes are described by spectral descriptors 74 and 84 that cluster near each other in plot 44. Conversely, spectra 62 and 72 with dissimilar shapes will be described by spectral descriptors 64 and 74 located distant from each other in spectral plot 44.

In an embodiment, and referring to FIGS. 3 and 4, the spectral descriptor method is used as a primary screening tool. For example, in one aspect, a plurality of reactions testing new catalysts are assembled in wells on a microtiter plate 50 (step a). Generally, at least one control, or known catalyst 80 is included in the experimental group. For each reaction, a spectrum is generated and scaled relative to the database (steps a–c), and principal component scores generated by projecting spectra for the new samples into the coordinate system defined by the original database (step d). Spectral descriptors for the new catalysts are plotted, and the plot used to visually or automatically determine whether any spectra from the new catalysts fall inside regions of the plot known to correlate with high molecular weight and/or low Fries (step e). Preferably, a new catalyst 100 that behaves similar to known catalyst 80 from the database will have a spectral descriptor 104 that is positioned near the spectral descriptor 84 for the known catalyst. Catalysts which meet predetermined threshold values of Fries products or polymer molecular weight are then passed along for secondary screening. In a preferred embodiment, a computer 56 automates the approach and provides plotting capability. For example, a computer program suitable for automating mapping is a MATLAB function.

Spectral descriptors can also be used for qualitative assessment of new catalyst performance without reference to a database of known spectra. For example, spectral mapping enables spectra generated as a function of catalyst loading (concentration) to be compared to control catalysts run in the same experiment. In an embodiment, a plurality of reactions testing new catalysts are assembled in wells on a microtiter plate. For each reaction set (e.g. each microtiter plate), control catalysts are included. Generally, an experimental set includes at least two control catalysts and six new catalysts, with each catalyst loaded at four replicates of three different concentrations.

For each reaction, a spectrum is generated and the spectra scaled, as for example, to a relative intensity of 1.0 at 500 nm. After mean-centering or auto-scaling the data, the principal components for the reaction set are computed, and principal component scores for each sample generated by projecting spectra for each reaction into the two-dimensional principal component coordinate system defined for that individual reaction set. Preferably, scores for replicate wells are averaged before plotting. Alternatively, non-linear mapping may be used to optimize the projection of the spectra and generation of the spectral descriptor scores.

Figure 5:
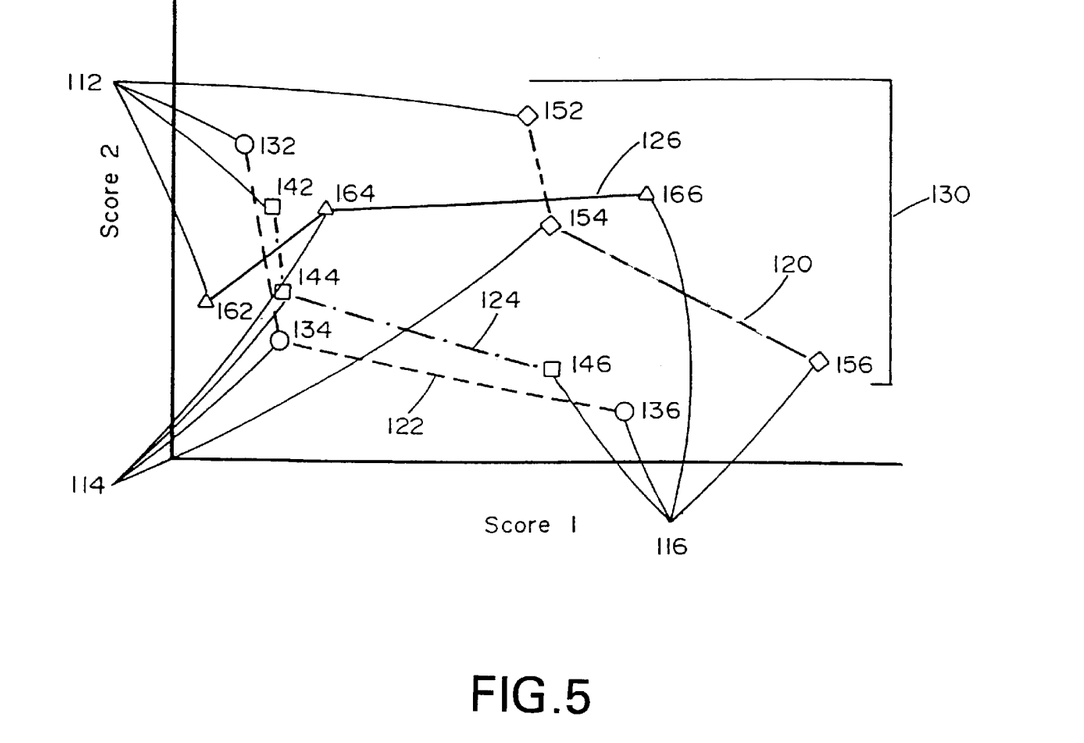
FIG. 5 is a representation of an embodiment of the method of spectral mapping.

Referring now to FIG. 5, in an embodiment, each catalyst is tested at multiple different loadings (concentrations), as for example loadings 112, 114 and 116 shown for catalysts 120, 122, 124 and 126. Preferably, at least one control catalyst 124 is included in the reaction set. For example, control catalysts may be those known to produce high molecular weight products and high levels of Fries, such as sodium hydroxide (NaOH), or catalysts known to produce polymers of low molecular weight and low Fries such as calcium acetate ($Ca(OAc)_2$). Generally, spectral descriptors for each concentration of a catalyst are linked together to generate a linear spectral shape map 130 characteristic of the catalyst.

Interpretation of spectral shape maps preferably utilizes knowledge of the control catalysts. Preferably, spectra that are similar in shape have similar spectral descriptor scores, and catalysts which generate products with similar properties (such as Fries products and polymer molecular weight) as a function of catalyst loading will generate similar spectral maps. Thus, the position and shape of the spectral shape map for a catalyst provides information as to whether a new catalyst 122 behaves like the control 124. More preferably, catalysts 122 and 124 that display similar efficacy and selectivity will have spectral descriptors 132, 134 and 136, and 142, 144 and 146, respectively, that line up near each other. Catalysts 120 and 126 which have different efficacy and selectivity preferably have spectral descriptors 152, 154 and 156, and 162, 164 and 166, respectively, which do not comprise similar shaped maps. Thus, in a preferred embodiment, the analyst can quickly screen several experiments to get a qualitative view of how multiple new catalysts performed without having to assemble a database of spectra previously characterized for Fries and molecular weight.

In another aspect, the method utilizes sample fluorescence to provide a quantitative assessment of reaction parameters. In an embodiment, the spectrum from an experimental sample is directly compared to spectra from a database. Database spectra which are similar in shape are identified, and a quantitative "prediction" of reaction parameters for the experimental sample made. Alternatively, database spectra are used to develop a multivariate mathematical model to correlate spectra to the reaction parameters of interest. The model is then applied to spectra from experimental samples testing new catalysts to obtain "predicted" values for selected reaction parameters. Preferably, the database is compiled from polymer samples covering a wide range reaction parameters of interest such as polymer molecular weight and Fries products. More preferably, the calibration methods include, but are not limited to, Euclidean distance minimization, locally weighted regression modeling, generalized regression neural network modeling, partial least squares regression, back propagation neural network, radial basis function neural network, and the like.

In an embodiment, the method employs "data mining" techniques for the direct comparison of spectra from new samples to a database of spectra previously collected from samples having a wide range of Fries products and molecular weight. The data mining method comprises two general phases: (I) database assembly, whereby spectra from a database of samples representative of a wide range of Fries values and molecular weight are assembled; and (II) primary screening, whereby spectra from new samples are compared to the database, and values for Fries products and polymer molecular weight are "predicted" by finding database spectra with similar spectral features to the samples being predicted.

In one aspect, the method comprises model building for the quantitative assessment of sample Fries and molecular weight. The method generally comprises two phases: (I) model building, whereby spectra from a database of samples representative of a wide range of polymer molecular weight and Fries products are used to generate a model to correlate spectra to molecular weight and Fries; and (II) primary screening, whereby spectra from new samples are compared to the model and values for Fries and molecular weight predicted. In an embodiment, the method comprises the technique of locally weighted regression for the steps of model building. In an embodiment, the method comprises the technique of using a Generalized Regression Neural Network (GRNN) for the steps of model building. GRNN is a nonlinear, non-parametric calibration algorithm which predicts analyte properties for a new spectrum by finding similar spectra in the database based on a distance metric and adjustable weighting factor. (See e.g., D. F. Specht, *IEEE Transaction on Neural Networks,* 2:568–576 (1988)). Because, GRNN modeling requires a substantial database, it has not been widely applied to chemical applications. Still, GRNN can provide increased flexibility in modeling.

In an embodiment, the method comprises the technique of using multivariate modeling techniques such as partial least squares regression, back propagation neural network, radial basis function neural network, and the like, to build a single mathematical model to relate the fluorescence spectra to a reaction parameter of interest, such as Fries products and/or molecular weight.

Figure 6:
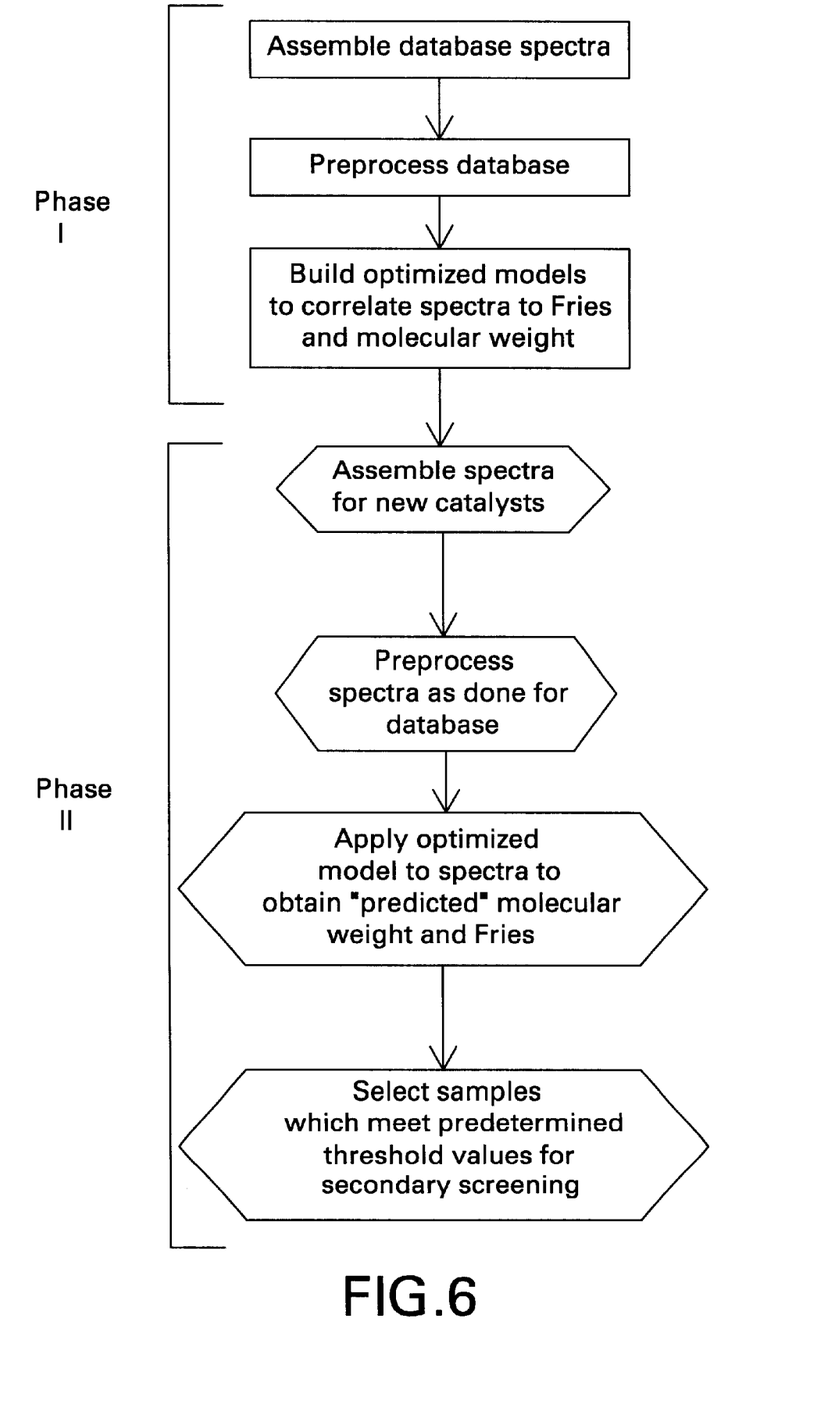
FIG. 6 is a schematic representation of an embodiment of the method comprising quantitative prediction of Fries and molecular weight using multivariate calibration methods.

Thus, referring to FIG. 6, model building (phase I) generally comprises the steps of: (1) assembling a database or calibration set of spectra using reaction samples covering a wide range of known Fries and molecular weight values; (2) if necessary, preprocessing the spectral database (as for example, normalization of spectra or auto-scaling or mean-centering the database); (3) building optimized models to correlate spectra to reaction parameters such as Fries and molecular weight. Once model building has been performed on a suitable database, primary screening (phase II) preferably comprises the steps of: (1) assembling spectra for new catalysts; (2) preprocessing each spectrum as was done for database; (3) applying the optimized model generated in phase I to obtain "predicted" reaction parameters, such as Fries products and/or polymer molecular weight for each of the new catalyst samples; and (4) selecting samples which meet a threshold for secondary screening.

As will be recognized by those of ordinary skill in the art, all or part of the steps in the method of the present invention may be coded or otherwise written in computer software, in a variety of computer languages including, but not limited to, C, C++, Pascal, Fortran, Visual Basic, Microsoft Excel, MATLAB, Mathematica, Java, and the like. Accordingly, additional aspects of the present invention include computer software for performing one or more of the method steps set forth herein. The software code may be compiled and stored in executable form on computer readable media as, for example, computer rom, floppy disk, optical disk, hard disks, cd rom, or the like.

For example, an embodiment of a system for performing the methods of the invention comprises at least one, but preferably, a plurality of polymer samples arranged as, for example, a microtiter tray. Samples are irradiated with excitation light of a predetermined wavelength and fluorescent light emitted from each of the samples monitored using a spectrofluorometer or other monitoring device.

EXAMPLE 1

Figure 7A:
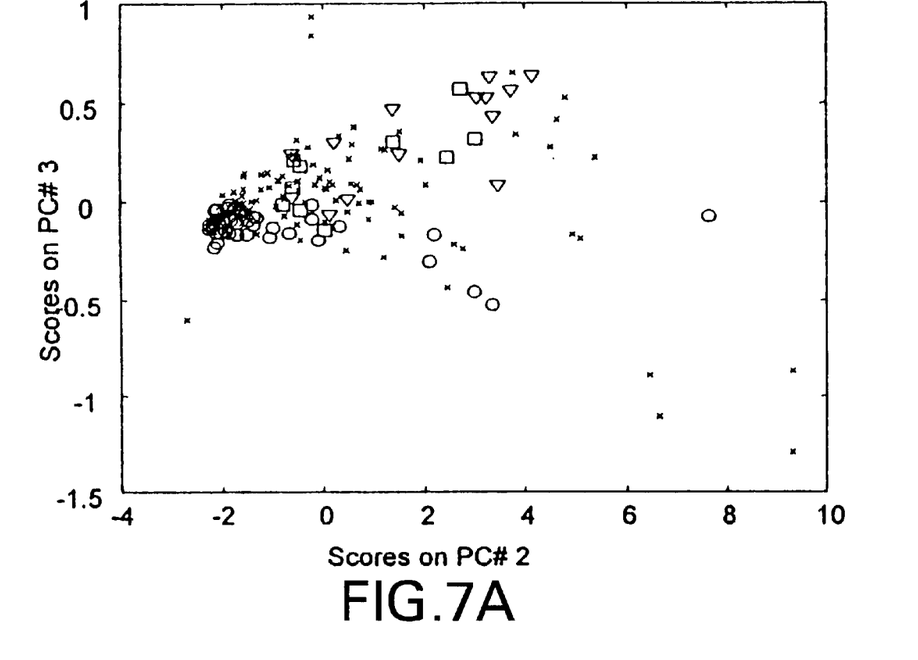
FIG. 7 illustrates an embodiment of the method comprising spectral plots from polymerization experiments run in a lab reactor (A,B) and microtiter plates (C,D)
Figure 7B:
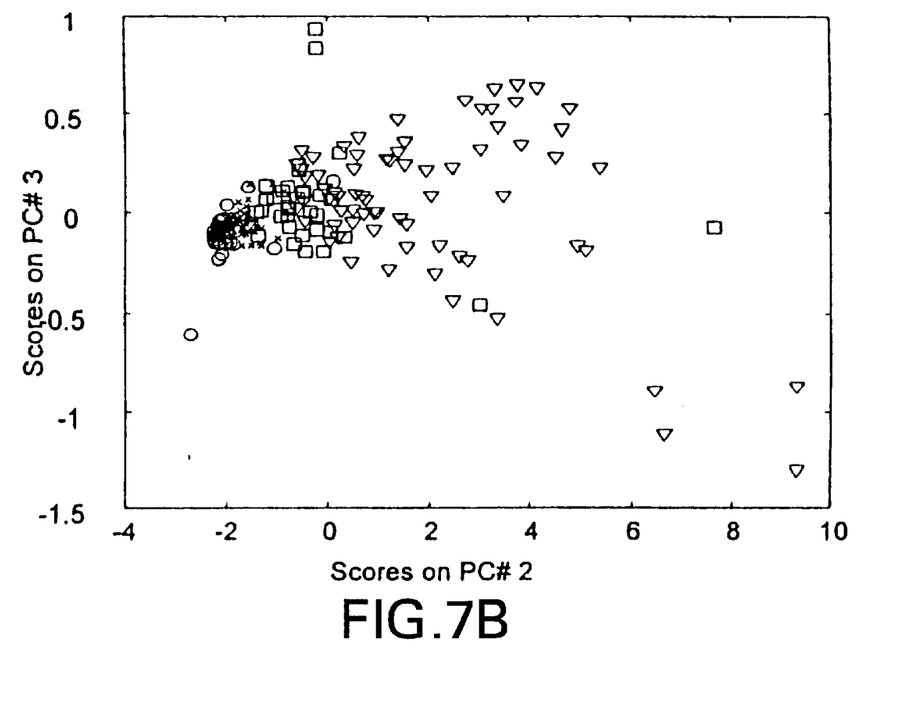
Figure 7C:
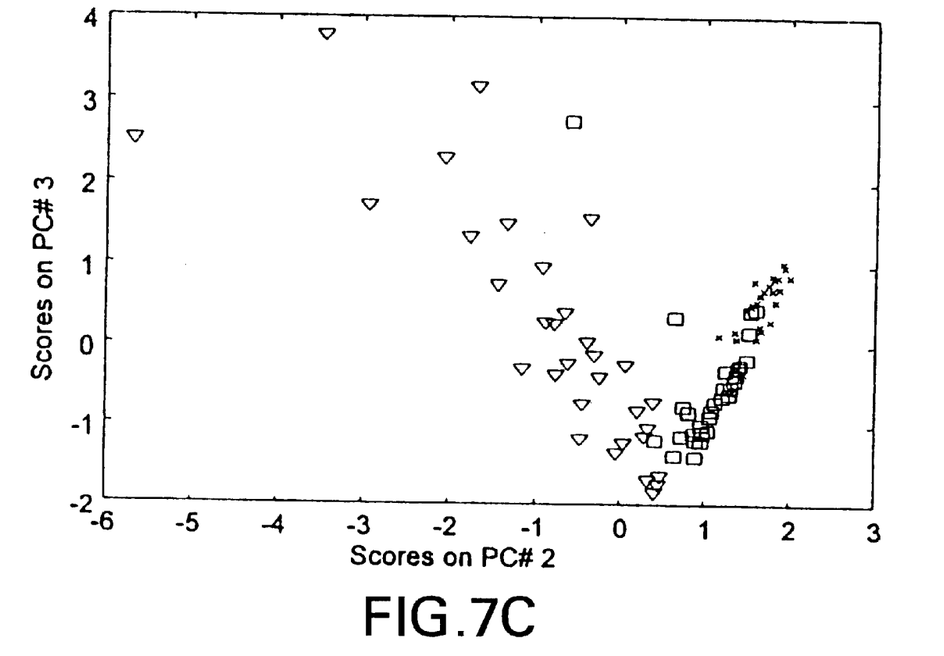
Figure 7D:
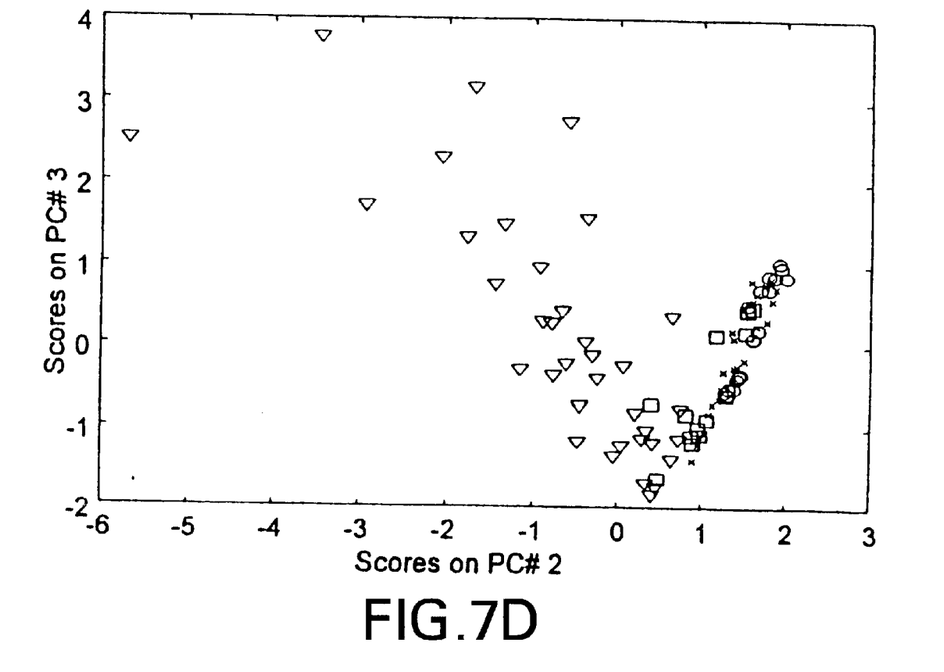

The use of principal component analysis (PCA) to generate a spectral descriptors plot was performed using polycarbonate LX resin samples produced in a lab-scale polymerization (FIGS. 7A and B) as well as samples produced in a microtiter plate reactor (FIGS. 7C and D). Measurements were performed on a setup which included a white light source (450-W Xe arc lamp, SLM Instruments, Inc., Urbana, Ill., Model FP-024), a monochromator for selection of the excitation wavelength (SLM Instruments, Inc., Model FP-092), and a portable spectrofluorometer (Ocean Optics, Inc., Dunedin, Fla., Model ST2000). The spectrofluorometer was equipped with a 200-$\mu$m slit, 600-grooves/mm grating blazed at 400 nm, which covered the spectral range from 250 to 800 nm with efficiency greater than 30%, and a linear CCD-array detector. Excitation light from the monochromator was focused into a "six-around-one" bifurcated fiber-optic reflection probe (Model R400-7-UV/VIS, Ocean Optics, Inc., Dunedin, Fla.) and fluorescence emission collected using the same probe. The second arm of the probe was coupled to the spectrofluorometer.

The method was initially validated on 194 polycarbonate samples from a lab-scale reactor having a reaction volume of about 1 liter. The samples included 85 catalysts at different concentrations and three (280° C., 295° C. and 310° C.) finishing processing temperatures. Reference values for polymer molecular weight (Mn) were measured relative to polycarbonate standards using size-exclusion chromatography. Reference values of Fries concentrations were measured using alkaline hydrolysis and high pressure liquid chromatography (HPLC).

Spectral data was collected from solid samples and arranged as an emission wavelength—fluorescence intensity response matrix. Analysis of data was performed using Principal Components Analysis with software from the PLS_Toolbox (Eigenvector Research, Inc., Manson, Wash.) operated with Matlab software (Mathworks Inc., Natick, Mass.). For the experiment shown, the data was autoscaled and second and third principal components plotted. For visualization on spectral plots, polymer molecular weight and Fries values were combined to fall in distinct ranges. Thus, results for polymer molecular weight (FIG. 7A) were grouped as follows: ($\triangledown$) 0–2500, (Y) 2500–5000, (x) 5000–9000, and (O) 9000–15000; results for Fries products (FIG. 7B) were grouped as follows: ($\triangledown$) 0–300, (Y) 300–800, (x) 800–2000, (O) 2000–8000 ppm.

It can be seen that each sample of polycarbonate is represented by a spectral descriptor which can be used for predicting material properties. For example, FIG. 7A demonstrates that an increase in the molecular weight of polymers is related to the angular distribution of the spectral descriptor scores around (−2, 0) in the PCA coordinate system. Further, a decrease in Fries concentration in the samples is described as the angular spread of the spectral descriptor scores from (−2, 0) to increasing values of principal component 2 (see FIG. 7B).

Similar findings are seen for an analysis of polymerization reactions performed in 96-well microtiter plate reactors having a reaction volume of about 100 ul. It can be seen that although the shapes of the spectral plots are different, samples of similar molecular weight (FIG. 7C) and Fries (FIG. 7D) cluster in distinct areas of the plot. Molecular weight ranges were grouped as follows: ($\triangledown$) 0–15000, (Y) 15000–23000, (x) 23000–32000, and (O) 32000–180000. Fries concentration ranges (ppm) were grouped as follows: ($\triangledown$) 0–2000, (Y) 2000–3000, (x) 3000–5000, and (O) 5000–7000 ppm.

EXAMPLE 2

The use of spectral shape mapping for the qualitative assessment of polymer molecular weight and Fries as a function of catalyst loading was evaluated. Principal component analysis was used to generate spectral descriptor scores, although nonlinear mapping may also be used. The spectral shape method enables comparison of spectra on a plate by plate basis (i.e. where one plate comprises an individual experiment testing several catalysts at several concentrations), without resource to a database of spectra characterized with respect to the reaction parameter of interest.

The experimental set included two control catalysts and six new catalysts, with each catalyst loaded at four replicates of three different concentrations. The two control catalysts, sodium hydroxide (NaOH) and calcium acetate ($Ca(OAc)_2$), are well characterized with respect to their ability to generate polymers comprising known molecular weight and Fries products. Sodium hydroxide is known to produce high molecular weight polymer and high levels of Fries products. Calcium acetate produces less Fries products, but also less high molecular weight polymer. If a new catalysts behaves similar to a control, the spectral descriptors for the new catalyst will be similar to the spectral descriptors for the control. Catalysts which generate polymer comprising high molecular weight and Fries as a function of catalyst concentration generally have a spectral shape descriptor similar to sodium hydroxide. Catalysts which generate polymer comprising low molecular weight and low Fries as a function of catalyst concentration generally have a spectral shape descriptor similar to calcium acetate.

Figure 8:
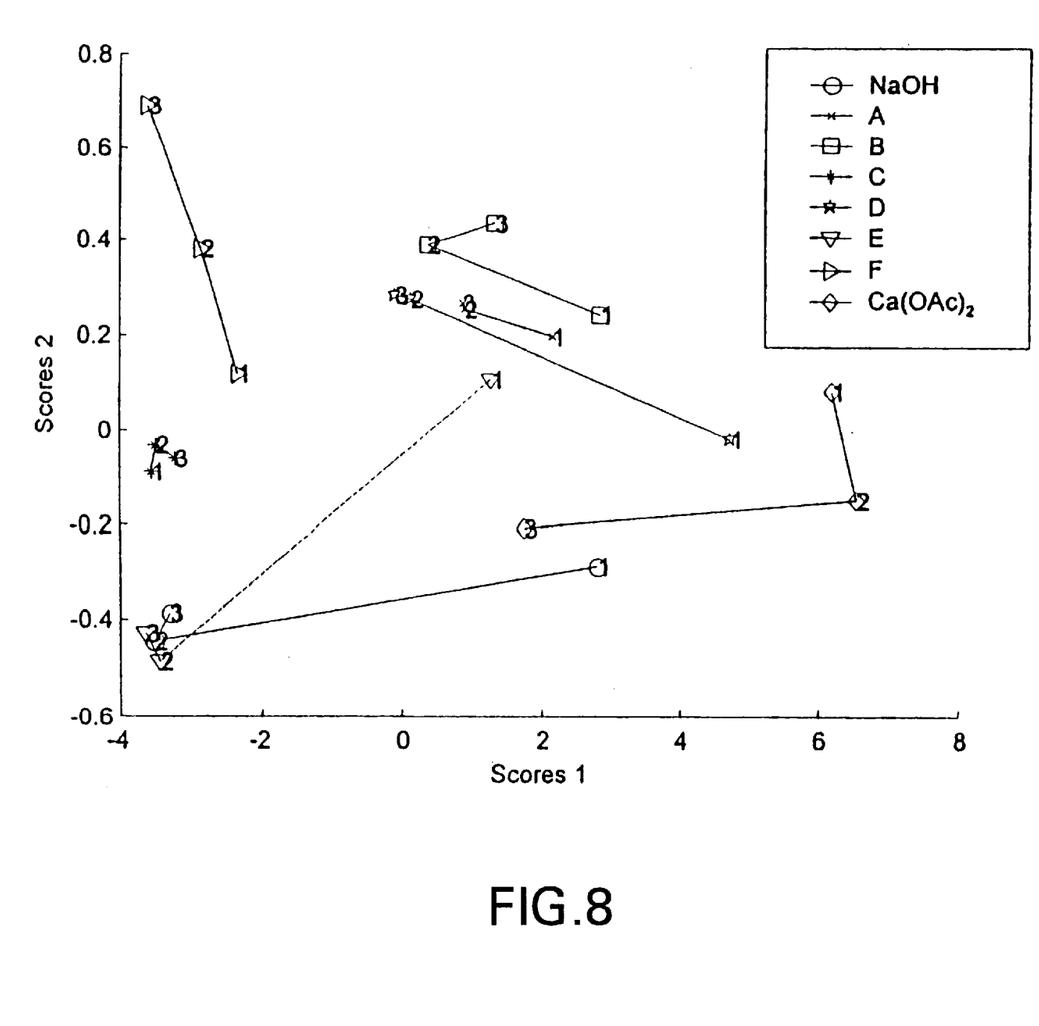
FIG. 8 illustrates an embodiment of the method comprising spectral shape maps for six test catalysts (1–6) and sodium hydroxide (NaOH) and calcium acetate (Ca(OAC)$_2$) controls.

FIG. 8 illustrates a spectral shape map for 95 fluorescence spectra for samples comprising six new catalysts (A–F) and the two control catalysts, sodium hydroxide (NaOH) and calcium acetate ($Ca(OAc)_2$). One spectrum (well #96) was discarded because that microreactor contained a thermocouple for temperature monitoring. Each catalyst was loaded at three different concentrations (1,2 and 3). Qualitative information is obtained about each of the new catalysts based on the spectral shape map. For example, it can be seen that the spectra from catalyst 3 change very little as a function of catalyst loading; this is often indicative of polymer gelling as a result of very high molecular weight and Fries. Catalyst 5 displays a profile which is similar to the sodium hydroxide control. Subsequent analysis verified that this catalyst generated polymer of high molecular weight polymer and high levels of Fries products. Notably, none of the catalysts in this experiment generated spectra which resembled spectra of materials generated with calcium acetate catalyst.

EXAMPLE 3

Nonlinear multivariate modeling is used to provide a quantitative prediction of Fries products and polymer molecular weight from sample fluorescence spectra. The use of data mining techniques for the quantitative prediction of polymer molecular weight and Fries products is shown in Table 1. Rather than developing a global model, data mining focuses on patterns or trends in the data that are locally dependent. Where spectral shape is dependent upon a specific reaction parameter, such as Fries or molecular weight, samples comprising similar spectral shapes are predicted to be similar with respect to that reaction parameter.

A program was written to perform a database search based on a Euclidean distance function to find the closest matching spectra in the spectral database to an individual spectrum under consideration. The program returns the Euclidean distance between the spectrum under consideration and the best matches (generally, the five best matches) from the database, and calculates predicted Fries and molecular weight values for the spectrum under consideration. The Euclidean distance function, for simplicity termed a "match factor", is zero for a perfect match and gets larger as the spectra become more dissimilar. Generally, match factors greater than 0.3 comprise relatively poor agreement between the test spectra and the database spectra.

The calibration set used to generate the database consisted of 1573 spectra from eighteen 96-well microtiter plate reactors. After collection of the spectra, the database samples were analyzed by conventional chemical techniques to obtain accurate values of Fries products and polymer molecular weight. The experimental (prediction) set consisted of five 96-well microtiter plate reactors. Samples in which polymer molecular weight could not be determined by conventional chemical techniques were not included.

All calculations were done in MATLAB 5.3 using in-house software and routines from the PLS Toolbox (Eigenvector, Inc., Manson, Wash.) on a personal computer. The predicted values were compared to values obtained by chemical analysis for polymer molecular weight and Fries products, and the root mean square relative standard error of prediction (RSEP) computed for each 96-well microtiter plate reactor. The relative standard error of prediction is expressed in percent as the standard error of prediction normalized by the maximum value of Fries and molecular weight, respectively. Table 1 displays the RSEPs for three calibration methods chosen for this application. These methods include data mining (DM), locally weighted regression (LWR), and generalized regression neural network (GRNN). Given the wide range of values for polymer molecular weight and Fries products for the database, these RSEP values are acceptable for primary screening.

TABLE 1

Relative Standard Errors of Prediction (RSEP, %) for Three Calibration Methods

| 96-well microtiter plate reactor # | Fries | | | Molecular Weight | | |
| --- | --- | --- | --- | --- | --- | --- |
| | DM | LWR | GRNN | DB | LWR | GRNN |
| 92 | 5.7 | 5.9 | 5.7 | 24 | 22 | 22 |
| 93 | 2.4 | 6.2 | 2.6 | 4.2 | 5.1 | 2.7 |
| 94 | 1.2 | 1.9 | 0.9 | 5.0 | 5.5 | 2.5 |
| 95 | 0.8 | 4.8 | 1.7 | 5.3 | 5.0 | 3.4 |
| 96 | 3.5 | 8.1 | 3.4 | 5.3 | 6.4 | 5.0 |

EXAMPLE 4

Results for quantitative estimation of molecular weight and Fries products by locally weighted regression (LWR)

are also shown in Table 1. Using the calibration database of 1573 spectra from eighteen 96-well microtiter plate reactors, LWR model parameters were optimized. As will be recognized by those of ordinary skill in the art, optimized parameters are specific for the particular dataset and application. Based on cross-validation analysis, the best LWR model for this dataset consisted of 3 principal components and 25 spectra for each local model.

The optimized LWR model was then applied to the experimental (prediction) set. The experimental (prediction) set consisted of five 96-well microtiter plate reactors. Samples in which polymer molecular weight could not be determined by conventional chemical techniques used in secondary screening were not included. All calculations were performed in MATLAB 5.3 using in-house software and routines from the PLS Toolbox (Eigenvector, Inc., Manson, Wash.) on a personal computer. As described for data mining (Example 3), predicted values for polymer molecular weight and Fries were compared to values obtained by chemical analysis, and the root mean square relative standard error of prediction (RSEP) computed for each plate (Table 1; LWR). Given the wide range of values for polymer molecular weight and Fries products for the database the SEP values are acceptable for primary screening.

EXAMPLE 5

Results for quantitative estimation of molecular weight and Fries products using a generalized regression neural network (GRNN) are also shown in Table 1. The GRNN model optimization was performed using the calibration database consisting of 1573 spectra from eighteen different 96-well microtiter plate reactors. The optimal GRNN configuration used a sigma (kernel width) of 0.8 and contained 1 hidden node for each spectrum in the data base.

The optimized GRNN model was then tested against the prediction set of five 96-well microtiter plate reactors. Samples in which polymer molecular weight could not be determined by conventional chemical techniques used in secondary screening were not included. All calculations were performed in MATLAB 5.3 using in-house software and routines from the PLS Toolbox (Eigenvector, Inc., Manson, Wash.) on a personal computer. Predicted values for polymer molecular weight and Fries were compared to values obtained by chemical analysis, and the root mean square relative standard error of prediction (RSEP) computed for each plate (Table 1). Given the wide range of values for polymer molecular weight and Fries products for the database the SEP values are more than acceptable for primary screening.

Figure 9:
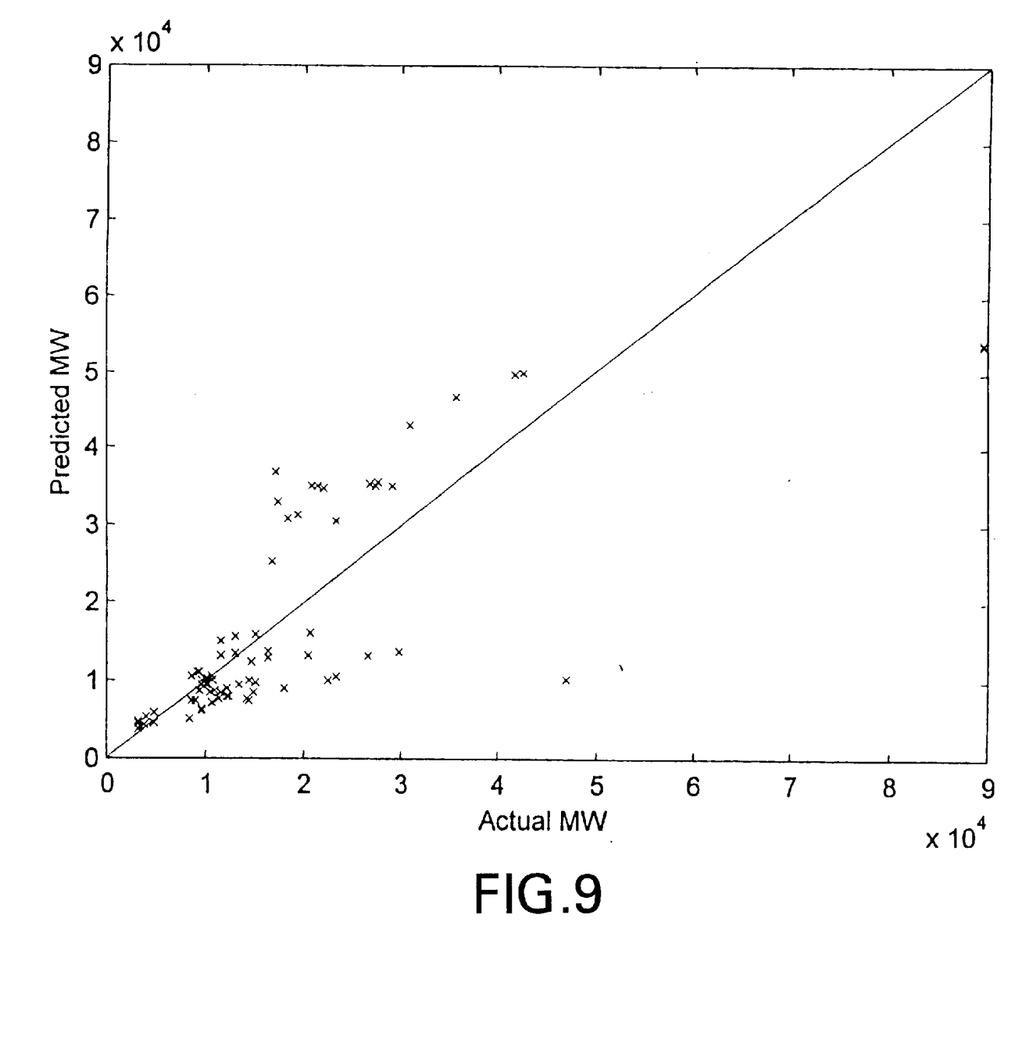
FIG. 9 illustrates an embodiment of the method of using generalized regression neural network (GRNN) modeling to provide predicted values of sample molecular weight.

An example illustrating the correlation between predicted polymer molecular weight and actual polymer molecular weight for one experimental plate is shown as FIG. 9. In this correlation plot, a unity line has been drawn to illustrate the perfect model. It can be seen that the actual values are well correlated to the predicted values based on GRNN modeling. In practice, for primary screening purposes, scatter of this magnitude is acceptable.

It will be recognized by those in the art that advantages of the fluorescence method disclosed here over other methods for the screening of potential catalysts and reaction conditions include:

1. Rapid qualitative and quantitative assessment of reaction parameters such as Fries products and/or polymer molecular weight;
2. Rapid assessment of catalyst efficiency;
3. Rapid assessment of catalyst selectivity;
4. Short analysis time;
5. Non-destructive and non-contact analysis in that measurements are performed with solid polymer without destruction of sample; and
6. High-throughput analysis capable of automation.

It will be understood that each of the elements described above, or two or more together, may also find utility in applications differing from the types described herein. While the invention has been illustrated and described as embodied in a method for high-throughput chemical screening, it is not intended to be limited to the details shown, since various modifications and substitutions can be made without departing in any way from the spirit of the present invention. For example, robotic equipment can be used to prepare the samples and various types of parallel analytical screening methods can be incorporated. Also, it is contemplated that other parameters besides Fries products and polymer molecular weight can be assessed using the techniques described herein. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A method for screening polymerization reactants, catalysts or reaction conditions, comprising:

irradiating at least one reaction sample (2) comprising fluorescence emitting Fries products with light of a defined excitation wavelength (4);

monitoring a fluorescence spectrum (10) emitted from the Fries products of the sample (2) by computing principal components of spectra emitted from the irradiated sample;

comparing the monitored fluorescence spectrum (10) to a database that comprises a Fries product fluorescence spectrum correlated with a reaction parameter of interest to determine a correlation between the monitored fluorescence spectrum (10) and the database Fries product fluorescence spectrum;

determining a reaction parameter of interest of the irradiated reaction sample from the correlation; and correlating the reaction parameter of interest with a performance of the polymerization reactants, catalysts or reaction condition.

2. The method of claim 1, wherein the reaction parameter comprises polymer average molecular weight.

3. The method of claim 1, wherein the excitation wavelength (4) is in the range of about 200 to 550 NM.

4. The method of claim 1, wherein the excitation wavelength (4) is in the range of about 300 to 470 NM.

5. The method of claim 1, wherein the excitation wavelength (4) is in the range of about 310 to 350 NM.

6. The method of claim 1, wherein the excitation wavelength (4) is in the range of about 340 NM.

7. The method of claim 1, wherein the emitted fluorescence spectrum (10) comprises more than two discrete wavelengths.

8. The method of claim 1, wherein the monitored fluorescence (16) is in the range of about 200 to about 900 NM.

9. The method of claim 1, wherein the monitored fluorescence spectrum (10) is in the range of about 260 to about 800 NM.

10. The method of claim 1, wherein spectral descriptor scores (66,68) for an individual sample (60) are derived by projection of the sample spectrum 10 onto the principal components for the database (40).

11. The method of claim 10, wherein the spectral descriptors (152, 154, 156) derived for reaction samples comprising a common catalyst (120) are linked to generate a spectral map (130).

12. The method of claim 1, wherein one reaction parameter of interest comprises polymer molecular weight.

13. The method of claim 1, further comprising multivariate calibration methods for the quantitative prediction of reaction parameters of interest.

14. The method of claim 13, wherein at least one reaction parameter of interest comprises polymer molecular weight.

15. The method of claim 13, wherein at least one reaction parameter of interest comprises Fries products.

16. The method of claim 13, further comprising the steps of:

assembling a database of spectra for reaction samples comprising a range of at least one reaction parameter of interest;

using multivariate calibration to generate a model correlating the database spectra to at least one selected reaction parameter of interest; and using the model to derive a predicted value for at least one of the selected reaction parameters for a new reaction sample.

17. The method of claim 16, wherein the multivariate calibration method comprises data mining methods for finding database spectra with minimal Euclidean distance to the sample spectrum.

18. The method of claim 16, wherein the multivariate calibration method comprises locally weighted regression.

19. The method of claim 16, wherein the multivariate calibration method comprises a generalized regression neural network.

20. The method of claim 16, wherein the multivariate calibration method comprises partial least squares regression.

21. Computer readable media comprising software code for performing the method of claim 1.

22. A method for screening polymerization reactants, catalysts or reaction conditions comprising:

irradiating a plurality of reaction samples (2) with light of a defined excitation wavelength (4);

monitoring fluorescence emitted (6) from each of the samples (2);

determining principal fluorescence components of the monitored fluorescence;

comparing the fluorescence components for each of the plurality of samples (2) to the fluorescence emission (18) from a database of reactions, wherein the database reactions have been characterized with respect to molecular weight of polymer product and amount of Fries products;

correlating the fluorescence observed (16) for each sample (2) to Fries products and polymer molecular weight.

23. The method of claim 22, further comprising an excitation wavelength in the range of about 200 to 550 nm.

24. The method of claim 22, further comprising an excitation wavelength in the range of about 300 to 470 nm.

25. The method of claim 22, further comprising an excitation wavelength in the range of about 310 to 350 nm.

26. The method of claim 22, further comprising an excitation wavelength of about 340 nm.

27. The method of claim 22, wherein the emitted fluorescence comprises more than two discrete wavelengths.

28. The method of claim 22, further comprising monitoring a spectrum of fluorescent radiation for each sample.

29. The method of claim 28, wherein the monitored emitted radiation is in the range of about 200 to about 900 nm.

30. The method of claim 28, wherein the monitored emitted radiation is in the range of about 260 to about 800 nm.

31. The method of claim 28, further comprising computing principal components correlated with polymer molecular weight and Fries products.

32. The method of claim 31, wherein spectral descriptor scores for new samples are derived by projection of spectra for the new samples onto the principal components for a database characterized with respect to polymer molecular weight and Fries products.

33. The method of claim 31, wherein the spectral descriptor scores derived for reaction samples comprising a test catalyst are linked to generate a spectral map which is compared to a similarly generated descriptor score for a control catalyst.

34. The method of claim 28, further comprising multivariate calibration methods for the quantitative prediction of polymer molecular weight and Fries products.

35. The method of claim 34, further comprising the steps of:

assembling a database of spectra from samples comprising a range of polymer molecular weight and Fries products;

generating a multivariate model correlating the database spectra to polymer molecular weight and Fries products; and using the model to derive a predicted value for the sample polymer molecular weight and Fries products.

36. The method of claim 35, wherein the multivariate calibration method comprises data mining methods for finding the database spectra with the minimum Euclidean distance to the sample spectrum.

37. The method of claim 35, wherein the multivariate calibration method comprises locally weighted regression.

38. The method of claim 35, wherein the multivariate calibration method comprises generalized regression neural networks.

39. The method of claim 35, wherein the multivariate calibration method comprises partial least squares regression.

40. Computer readable media comprising software code for performing the method of claim 22.

* * * * *